United States Patent [19]

Frischinger et al.

[11] Patent Number: 6,136,922
[45] Date of Patent: *Oct. 24, 2000

[54] COMPOSITION OF CARBOXYL-CONTAINING POLY(METH)ACRYLATE, CARBOXYL-TERMINATED POLYESTER AND EPOXY RESIN

[75] Inventors: Isabelle Frischinger, Riespach, France; Jacques-Alain Cotting, Bonnefontaine, Switzerland; Jacques François, Huningue, France

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/690,373

[22] Filed: Jul. 26, 1996

Related U.S. Application Data

[63] Continuation of application No. 08/508,146, Jul. 27, 1995, abandoned.

[30] Foreign Application Priority Data

Aug. 2, 1994 [CH] Switzerland ............... 2417/94

[51] Int. Cl.[7] ............... C08K 5/07; C08L 33/02
[52] U.S. Cl. ............... 525/111; 523/454
[58] Field of Search ............... 525/111; 523/454

[56] References Cited

U.S. PATENT DOCUMENTS

| | | | |
|---|---|---|---|
| 3,444,237 | 5/1969 | Jaffe | 260/468 |
| 3,859,314 | 1/1975 | Dukes et al. | 260/348.6 |
| 3,954,712 | 5/1976 | Lottanti et al. | 260/47 |
| 4,667,044 | 5/1987 | Nees et al. | 549/539 |
| 4,871,806 | 10/1989 | Shalati et al. | 525/111 |
| 4,988,767 | 1/1991 | Pettit, Jr. | 525/111 |
| 5,283,290 | 2/1994 | Jung et al. | 525/111 |
| 5,322,907 | 6/1994 | Cotting et al. | 525/438 |

FOREIGN PATENT DOCUMENTS

| | | |
|---|---|---|
| 0212457 | 3/1987 | European Pat. Off. . |
| 0263429 | 4/1988 | European Pat. Off. . |
| 0330887 | 9/1989 | European Pat. Off. . |
| 4237658 | 5/1994 | Germany . |
| 2160534 | 12/1985 | United Kingdom . |

OTHER PUBLICATIONS

Chemical Abstr. 121: 258049t of DE 4,237,658, May 1994.
Derwent Abstr. 94–159946/20 of DE 4,237,658, May 1994.

*Primary Examiner*—Robert E. Sellers
*Attorney, Agent, or Firm*—David R. Crichton; Michele A. Kovaleski

[57] ABSTRACT

A curable composition comprising
A) a mixture of
A1) at least one polymer based on acrylate and/or methacrylate monomers and containing on average 0.1 to 4.0 equivalents of free carboxyl groups per kilogram of polymer, and
A2) at least one carboxyl-terminated polyester which contains on average
0.2 to 6 equivalents of free carboxyl groups per kilogram of polyester
such that component A1) constitutes 50 to 90% by weight, and component A2) makes up the remainder, of the mixture A;
B) an epoxy resin containing 2 or more epoxy groups per molecule, selected from;
glycidyl esters of cyclic carboxylic acids,
glycidyl ethers of trimethylolpropane,
glycidyl ethers of bis(dimethylolpropyl) ether, and
reaction products of glycidyl ether derivatives of trimethylolpropane or bis(dimethylolpropyl) ether with aliphatic or cycloaliphatic polyisocyanate monomers or oligomers, or a mixture of two or more than two of these epoxy resins;
C) a catalyst for speeding up the thermal reaction of epoxy and carboxyl groups, and
D) an inert solvent;
the molar ratio of free carboxyl groups to epoxy groups in said composition being 0.3:1 to 3:1, and said composition containing, except for component B, no components carrying epoxy groups. The composition is generally suitable as coating agent, especially as lacquer for coating automobile parts.

5 Claims, No Drawings

COMPOSITION OF CARBOXYL-CONTAINING POLY(METH)ACRYLATE, CARBOXYL-TERMINATED POLYESTER AND EPOXY RESIN

This application is a continuation of application Ser. No. 08/508,146, filed Jul. 27, 1995, now abandoned.

The present invention relates to compositions that are suitable in particular for use as automomobile lacquers and especially relates to curable compositions based on polymers containing free carboxyl groups and epoxy resins. The invention further relates to novel glycidyl esters and mixtures of glycidyl esters which are particularly suitable for the said compositions and to a process for coating objects using these compositions.

Coloured and clear lacquer systems frequently used In practice are based on 2-component mixtures comprising polyols such as polyester polyols, polyurethane polyols or polyols based on acrylates, and polyisocyanates as hardeners. The polyisocyanates, however, are difficult to handle, sensitive to moisture, and ensure only a short pot life for the lacquers. Furthermore, special precautions must be taken on account of the toxicity of the isocyanates.

Other curable compositions based on polyepoxides, halfesters of diols and polycarboxylic anhydrides are disclosed in U.S. Pat. No. 3,954,712.

Curable compositions based on polymers containing free carboxyl groups and epoxy resins, and the use thereof as automobile lacquers are disclosed in EP-A-0 212 457. These compositions may comprise as carboxyl group-containing polymer component, inter alia, a mixture of a polymer based on acrylate and/or methacrylate monomers and preferably containing 0.54 to 2.7 equivalents of free carboxyl groups per kilogram of polymer and having a $T_g$ value below 30° C., and/or a carboxyl-terminated polyester which contains c. 0.2 to 2.1 equivalents of free carboxyl groups per kilogram of polyester and likewise has a $T_g$ value below 30° C. EP-A-0 212 457 cites as suitable epoxy resins, in addition to the preferred epoxy acrylates, glycidyl ethers of aliphatic and of aromatic polyhydroxy compounds preferably containing more than one epoxy group and up to three epoxy groups per molecule as well as difunctional cycloaliphatic epoxy resins, i.e. compounds containing two epoxycycloalkyl groups. The claimed curable compositions have a molar ratio of free carboxyl groups to epoxy groups of 0.3:1 to 3:1 and may contain as further components, inter alia, suitable catalysts for speeding up the reaction of epoxy components with carboxylate components, as well as suitable inert solvents.

The coatings based on the compositions referred to above are still capable of improvement, especially with respect to their hardness, flexibility, resistance to organic liquids, e.g. petroleum spirit, and their weather resistance.

Accordingly, the invention relates to a curable composition comprising the following components:
A) a mixture of
A1) at least one polymer based on acrylate and/or methacrylate monomers and containing on average 0.1 to 4.0 equivalents of free carboxyl groups per kilogram of polymer, and
A2) at least one carboxyl-terminated polyester which contains on average
0.2 to 6 equivalents of free carboxyl groups per kilogram of polyester
such that component A1) constitutes 50 to 90% by weight, and component A2) makes up the remainder, of the mixture A;

B) an epoxy resin containing 2 or more epoxy groups per molecule, selected from;
polyglycidyl esters of cyclic polycarboxylic acids,
polyglycidyl ethers of trimethylolpropane,
polyglycidyl ethers of bis(dimethylolpropyl) ether, and
reaction products of polyglycidyl ether derivatives of trimethylolpropane or bis(dimethylolpropyl) ether with aliphatic or cycloaliphatic polyisocyanate monomers or oligomers, or a mixture of two or more than two of these epoxy resins;
C) a catalyst for speeding up the thermal reaction of epoxy and carboxyl groups, and
D) an inert solvent;
the molar ratio of free carboxyl groups to epoxy groups in said composition being 0.3:1 to 3:1, and said composition containing, except for component B, no components carrying epoxy groups.

The compositions of this invention are highly reactive and form coatings of particular hardness and resistance to solvents. The coatings also have the additional properties of good fastness to weathering, elasticity and impact strength. The compositions can also be prepared with a high solids content, typically of 45% by weight and more, and hence with a correspondingly low content of solvent. Even with such high solids contents, the compositions of this invention have a very low viscosity. Thus correspondingly high-solids paints can be prepared from the novel compositions whose spray viscosity corresponds to a flow time of 18 seconds (No. 4 DIN cup).

The epoxy resins useful for the novel compositions conveniently have a molecular weight of c. 200 to 2000. It is, of course, also possible to use mixtures of two or more than two of the cited epoxy resins.

Glycidyl esters of cyclic carboxylic acids will be understood as meaning in the context of this invention polyglycidyl esters of carboxylic acids which contain at least two carboxyl groups which are attached to ring systems of the carboxylic acid molecule. These carboxylic acids may have only one ring system of preferably 5 to 14 ring carbon atoms, typically polycarboxylic acid derivatives of benzene or naphthalene. They may, however, also contain two or more such ring systems in their molecule which are linked through suitable groups of atoms, for example a group of formula
—CH$_2$—, —C(CH$_3$)$_2$—, —O— or

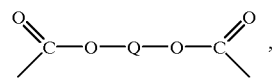

wherein Q is a divalent organic radical of 2 to 15 carbon atoms.

The polyglycidyl esters suitable for use in this invention typically comprise polyglycidyl esters of cyclic polycarboxylic acids, e.g. dicarboxylic acids such as phthalic acid, isophthalic acid, terephthalic cid, 2,5-dimethylphthalic acid, naphthalene-2,6-dicarboxylic acid, naphthalene-1,8-dicarboxylic acid, naphthalene-2,3-dicarboxylic acid, diphenyl ether-4,4'-dicarboxylic acid, diphenyl-2,2'-dicarboxylic acid, tetrachlorophthalic acid, 2,5-dichlorophthalic acid, o-, m- or p-phenylenediacetic acid, tetrahydrophthalic acid, methyltetrahydrophthalic acid, hexahydrophthalic acid, methylhexahydrophthalic acid, endomethylenehexahydrophthalic acid, hexahydroterephthalic acid, hexahydroisophthalic acid, thiophene-2,5dicarboxylic acid, furan-2,5-dicarboxylic acid, furan-3,4-dicarboxylic acid, pyrazine-3,4-dicarboxylic acid, or of higher functional carboxylic acids such as 1,2,3-benzenetricarboxylic acid (hemimellitic acid), 1,2,4-benzenetricarboxylic acid (trimellitic acid), 1,3,5-benzenetricarboxylic acid (trimesic acid), 1,2,3,4-benzenetetracarboxylic acid (mellophanic acid), 1,2,4,5-benzenetetracarboxylic acid (pyromellitic acid), 1,2,3,5-benzenetetracarboxylic acid, benzenepentacarboxylic acid and benzenehexacarboxylic acid (mellitic acid), naphthalenetetracarboxylic acid, perylenetetracarboxylic acid or tetracarboxylic acids of formula

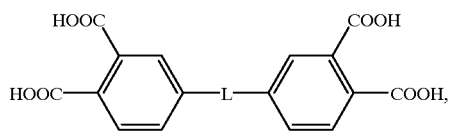

wherein L is —CH$_2$—, —C(CH$_3$)$_2$— or —O—, preferably benzophenone-3,3',4,4'-tetracarboxylic acid as well as derivatives of the cited acids. which contain partially or completely hydrogenated carbon rings.

The polyglycidyl esters can be prepared by known methods or by methods analogous thereto e.g. in accordance with U.S. Pat. No. 3,859,314, DE-A-31 26 411 or EP-A-506 617. Very particularly preferred polyglycidyl esters are the diglycidyl ester of cis-hexahydrophthalic acid as well as in particular the triglycidyl esters of trimellitic and hexahydrotrimellitic acid.

The reaction products of polyglycidyl ether derivatives of trimethylolpropane or bis(dimethylolpropyl) ether with aliphatic or cycloaliphatic polyisocyanate monomers and oligomers preferably have a molecular weight not higher than 2000 and comprise in particular the reaction products with diisocyanates or with their condensates such as urethdiones, carbodiimides, biurets or isocyanurates. Very suitable condensates are also the reaction products of the cited glycidyl ether derivatives with urethanised diisocyanates, i.e. with reaction products of diisocyanates with polyols, preferably with diols. Preferred diisocyanates are hexamethylene diisocyanate, trimethylhexamethylene diisocyanate, cyclohexane diisocyanate, methylene dicyclohexyldiisocyanate and, most preferably, with isophorone diisocyanate (3,5,5-trimethyl-1-isocyanato-3-isocyanatomethylcyclohexane) or the condensates thereof. Preferred glycidyl ether derivatives for the preparation of the reaction products are trimethylolpropane monoglycidyl ether, trimethylolpropane diglycidyl ether and trimethylolpropane triglycidyl ether or mixtures of these compounds. These mixtures preferably have an epoxy value from 3 to 7 eq/kg, most preferably from 4.5 to 6.75. The reaction products can be obtained in accordance with e.g. EP-A-0 263 429 by reacting the components in the temperature range from 70 to 110° C. and in the absence or presence of a catalyst, typically dibutyltin dilaurate, the components conveniently being used in such amounts that there is about one isocyanato group per hydroxyl group.

Preferred compositions contain an epoxy resin selected from the group consisting of cis-hexahydrophthalic acid diglycidyl ester, trimellitic acid triglycidyl ester, 1,2,4-cyclohexanetricarboxylic acid triglycidyl ester, trimethylolpropane triglycidyl ether, the reaction product of trimethylolpropane diglycidyl ether with isophorone diisocyanate and of trimethylolpropane triglycidyl ether with isophorone diisocyanate. Further preferred compositions are those wherein the epoxy resin is a reaction product of the diglycidyl ether of trimethylolpropane with a urethane, formed from isophorone diisocyanate and 1,4-bis(hydroxymethyl) cyclohexane which carries two isocyanato end groups. Such products have the following formula:

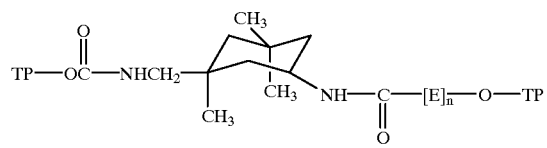

wherein E is a group of formula:

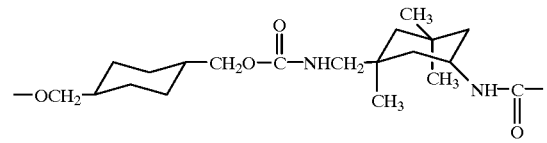

n is an integer from 1 to 5, and
TP is the radical of trimethylolpropane diglycidyl ether from which its hydroxyl group has been removed.

Particularly preferred epoxy resins on account of their good influence on the weather-resisance of coatings based on the novel compositions, as well as on account of their comparatively good reactivity are polyglycidyl esters of cyclohexanepolycarboxylic acid carrying more than two glycidyl ester groups, such as the triglycidyl esters of hexahydrotrimesic acid and, in particular, of hexahydrotrimellitic acid. Polylycidyl esters of cyclohexanepolycarboxylic acid carrying more than two glycidyl ester groups are novel and are likewise an object of this invention. They can be prepared in usual manner, for instance, by reacting the proper cyclohexane polycarboxylic acid with epichlorohydrine, and may also be used with advantage in admixture with polyglycidyl esters of aromatic carboxylic acids as components of novel compositions, the glycidyl esters of cyclohexane-polycarboxylic acid preferably making up 30 to 90% by weight, preferably 50 to 90% by weight, of the mixture.

Compositions containing polyglycidyl esters of cyclic carboxylic acids as epoxy resin constitute a preferred embodiment of the invention, as do likewise those compositions containing epoxy resins carrying three or more epoxy groups per molecule.

The polymer based on acrylate and/or methacrylate monomers and forming component A1) of mixture A of the claimed compositions is a copolymer of one or more than one acrylate and/or methacrylate, preferably the corresponding alkyl (meth)acrylates containing 1 to 8 carbon atoms in the alkyl moiety, with acrylic acid and/or methacrylic acid and further optional ethylenically unsaturated comonomers, and preferably has a molecular weight of 1000 to 30 000. Its glass transition temperature is expediently above 20° C., preferably above 30° C. Typical examples of (meth)acrylate monomers are ethyl acrylate, butyl acrylate, 2-ethylhexyl acrylate, as well as, in particular, C$_1$–C$_4$alkylmethacrylates such as methyl methacrylate, ethyl methacrylate or butyl methacrylate. (Meth)acrylate derivatives which contain silane groups may also be used. Suitable ethylenically unsaturated comonomers are typically acrylonitriles or methacrylonitriles as well as vinyl compounds. Preferred comonomers are aromatic vinyl compounds, preferably styrene. It is very particularly preferred to use a copolymer of methacrylic acid, C$_1$–C$_4$alkyl esters of methacrylic acid and styrene as component A1. The above polymers can be prepared in per se known manner, typically by polymerisation of the monomers dissolved in a suitable organic solvent, preferaby in toluene, or in a mixture of 1-methoxy-2- propanol, 1-methoxy-2-propylacetate and methyl isobutyl ketone (e.g. in the ratio 70/20/10), in the presence of a suitable initiator such as dicumyl peroxide, and of a chain-transfer agent, conveniently thioglycolic acid.

The carboxyl-terminated polyesters of component A2) conveniently have a molecular weight in the range from 500 to 5000, preferably up to 2000, most preferably up to 1000. Their glass transition temperature is preferably below 30° C., most preferably below 0° C. Such polyesters are free-flowing at room temperature.

Preferred polyesters of the indicated kind are half-esters of a polyester polyol or a polylactone polyol, each carying at least 2 hydroxyl end groups, and an aliphatic or cycloaliphatic 1,2-dicarboxylic acid. These half-esters have the following molecular structure:

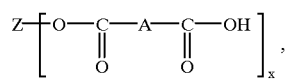

in which Z is the radical of a polyester or polylactone polyol of formula $Z(OH)_x$ without its hydroxyl end groups, A is the radical of a 1,2-carboxylic acid of formula $A(COOH)_2$ without its carboxyl groups in 1,2-position, with which or with whose ester-forming derivative the polyol has been reacted, and x is an integer of at least 2. The upper limit of x is preferably 4. Most preferably x is 2 or 3. Particularly preferred half-esters are those derived from succinic acid and, in particular, from cycloaliphatic carboxylic acids, preferably from hexahydrophthalic acid or hexahydrotrimellitic acid as acid component.

Polyester polyols which may be suitably used for the preparation of component A2) are reaction products of polyfunctional carboxylic acids, preferably cycloaliphatic or aliphatic carboxylic acids such as hexahydroisophthalic acid, hexahydroterephthalic acid, hexahydrophthalic acid, succinic acid, glutaric acid, adipic acid, pimelic acid, suberic acid, azelaic acid, sebacic acid, with an excess of aliphatic polyols, in particular di- and triols, typically ethylene glycol, propylene glycol, 1,3-butanediol, 1,4-butanediol, neopentanediol, isopentyl glycol, 1,6-hexanediol, 1,7-heptanediol, 1,8-octanediol, glycerol, trimethylolethane, trimethylolpropane or cyclohexanediol. Linear aliphatic dicarboxylic acids as well as linear aliphatic diols each containing 5 to 8 methylene groups in the aliphatic chain are preferred. Polyesters of this kind are also commercially available, e.g. from King Industries under the registered trademark K-Flex® 188 and 148.

To prepare component A2) of the compositions of this invention there may also be suitably used as polyols $Z(OH)_x$ specific polylactone polyols, namely compounds of formula

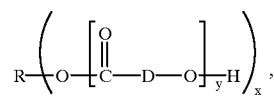

wherein R is the radical of a cyclic or acyclic polyol $R(OH)_x$ of valency x without its hydroxyl groups, which polyol is used as initiator for the lactone polymerisation, x is as previously defined above in connection with x, y is 1 or an integer greater than 1, preferably from 1 to bis 20, most preferably from 1 to 10, and D corresponds to an alkylene group of structure

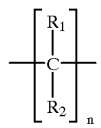

containing a maximum number of 12 carbon atoms and wherein $R_1$ and $R_2$ are each independently of the other a hydrogen atom or a $C_1$–$C_3$ alkyl radical, and n is an integer from 5 to 8. Polylactones of the indicated type are known and described, inter alia, in GB-A-2 160 534, the contents of which are incorporated herein by reference. Most preferably n is 5 and $R_1$ and $R_2$ are each a hydrogen atom. Such polycaprolactones are also commercially available from Interox Chemicals Ltd. under the registered trademark CAPA®.

The most preferred carboxyl-terminated polyesters are the half-esters of hydroxyl-terminated polycaprolactones and cis-hexahydrophthalic anhydride.

The compositions of this invention additionally comprise a catalyst for speeding up the thermal reaction of epoxy and carboxyl groups. The catalyst makes possible a sufficiently rapid cure in the temperature range from 60 to 130° C. The catalyst is normally an organic amine or a derivative of an amine, preferably a tertiary amine or a nitrogen-containing heterocyclic compound. Preferred catalysts are N-benzyldimethylamine and 1,8-diazabicyclo[5,4,0]-7-undecene. The catalyst or a catalyst mixture is conveniently used in an amount of c. 0.5 to 10% by weight, preferably from 1 to 5% by weight.

Typical examples of suitable inert solvents are xylenes, butyl acetate, isobutanol, 1-methoxy-2-propanol, 1-methoxy-2-propylacetate and methyl isobutyl ketone (MIBK). It is particularly preferred to use a solvent mixture of 1-methoxy-2-propanol, 1-methoxy-2-propylacetate and MIBK, preferably in the weight ratio of c. 70:20:10. The novel compositions can be prepared with quite minor amounts of inert solvent and therefore preferably have a high solids content, conveniently in the range from 40 to 60% by weight for a spray viscosity of 18 seconds flow time, measured in a No.4 DIN cup.

In addition to comprising the cited components, the novel compositions may further comprise additional components ordinarily used for colour-coating finishes, typically including pigments, fluorescent whitening agents, light stabilisers, antioxidants, flow control agents, adhesives, thixotropic agents and the like.

The compositions of this invention may be used as coating agents, casting resins impregnating resins, laminating resins, adhesives or sealants. The particularly preferred utility of the novel compositions is for automobile finishes, typically as primer or, charged with pigments and/or dyes, as colour-coating primer as well as, in unpigmented form, as clear finishing lacquer. The novel compositions are especially suitable for original equipment manufacturing, preferably applying stoving temperatures in the range from c. 60 to 180° C. It is of particular advantage for the utility as finishing lacquer that the novel compositions should exhibit no yellowing tendency even at elevated stoving temperatures, for example of 130° C. and above.

Accordingly, the invention further relates to a process for coating objects, preferably automobile parts, which comprises coating the object with a novel composition, drying the coating and effecting a cure in the temperature range from 60 to 180° C., preferably from 80 to 130° C.

Unless otherwise indicated, percentages in the Examples are percentages by weight.

Identical footnotes pertaining to the Examples have identical meanings for all Examples, unless otherwise indicated.

EXAMPLE 1

Preparation of the Methacrylate Component 1

|  | Parts by weight [g] |
|---|---|
| Monomer feed: | |
| methacrylic acid (MAA) | 30 |
| styrene (St) | 20 |
| methyl methacrylate (MMA) | 30 |
| butyl methacrylate (BuMA) | 120 |
| dicumyl peroxide (initiator) | 3.0 |
| thioglycolic acid (chain-transfer agent) | 3.5 |
| Reactor charge: | |
| toluene | 60 milliliters |
| dicumyl peroxide (initiator) | 3.0 g |
| thioglycolic acid (chain-transfer agent) | 3.5 g |

The monomer mixture is first washed with an aqueous phase of 4% solution of sodium hydroxide and a 20% solution of sodium chloride and dried over anhydrous sodium sulfate.

The reactor charge is placed in a reactor fitted with mechanical stirrer, nitrogen sparge, condenser, heat control, thermometer and a metering pump for the continuous adition of the monomer mixture. While sparging the reactor with nitrogen, the temperature of the reactor is raised to 110° C. so that the toluene refluxes. The monomer mixture is then added to the mixture in the reactor over 3 hours. Towards the end of the addition there is a strong increase in the viscosity of the mixture in the reactor. The reaction mixture is heated for a further 6 hours to 110° C., and then cooled to room temperature. The toluene is removed by evaporation and the copolymer obtained as residue is dissolved in ether and precipitated in hexane. The precipitate is isolated by filtration and dried.

The resultant copolymer has a molecular weight ($M_w$) of 10 330 (determined by GPC using a polystyrene standard; $M_w/M_n$=4.7), a glass transition temperature ($T_g$) of 45.8° C., and contains 1.98 equivalents of free carboxyl groups per kilogram of copolymer.

EXAMPLE 2

Preparation of Methacrylate Component 2

The procedure of Example 1 is repeated, except that the reactor contains instead of toluene a solvent mixture consisting of 70% of 1-methoxy-2-propanol, 20% of 1-methoxy-2-propylacetate and 10% of methyl isobutyl ketone (LMGXI mixture). Unlike the toluene in Example 1, this solvent mixture is not removed, but is used to adjust the solution of the copolymer obtained after cooling the reaction mixture to a solids content of 54.6%. This solution then has a viscosity of 460 mPa·s at 25° C.

The resultant copolymer has a molecular weight ($M_w$) of 4 300 (determined by GPC using a polystyrene standard; $M_w/M_n$=3.0), a glass transition temperature ($T_g$) of 22° C. and contains 1.80 equivalents of free carboxyl groups per kilogramm of copolymer.

EXAMPLE 3

Preparation of the Methacrylate Component 3

|  | Parts by weight [g] |
|---|---|
| Monomer mixture: | |
| hydroxyethyl methacrylate | 30 |
| styrene (St) | 10 |
| methyl methacrylate (MMA) | 5,0 |
| butyl methacrylate (BuMA) | 60 |
| (3-trimethoxysilyl)propyl-methacrylate | 10,8 |
| dicumyl peroxide (initiator) | 2.7 |
| thioglycolic acid (chain-ransfer agent) | 3.2 |
| Reactor charge | |
| LMGXI mixture | 60 milliliters |
| Charge 2: | |
| LMGXI mixture | 40 milliliters |
| dicumyl peroxide (initiator) | 0.3 g |
| thioglycolic acid (chain-transfer agent) | 0.3 g |

The charge is added to a reactor as in Example 1 and, while sparging with nitrogen, heated to reflux. The monomer mixture is then added and the reaction mixture is refluxed for another 1.25 hours. The polymer solution has a solids content of 47.4%, the copolymer has a molecular weight ($M_w$) of 3407 (determined by GPC using a polystyrene standard; $M_w/M_n$=3.3).

63.3 g of the polymer solution and 0.361 g of tripropylamine are charged to a reactor and heated, under nitrogen, to 115° C. Then 6.106 g of cis-hexahydrophthalic anhydride are added and heating is continued for another 70 minutes. The resultant clear solution of the acrylate polymer containing free carboxyl groups (methacrylate component 3) has a solids content of 23.3% and a viscosity of c. 25 mPa·s. The molecular weight of the polymer ($M_w$) is 3917, and its carboxyl functionality is 0.32 eq/kg.

EXAMPLE 4

Preparation of a Half-Ester of a Polycaprolactone Polyol and Hexahydrophthalic Anhydride 59.97 grams (0.0389 moles) of hexahydrophthalic anhydride and 1.6 g of tetramethylammonium chloride are charged to a reactor fitted with mechanical stirrer, nitrogen sparge and thermometer, and the mixture is heated, under nitrogen, to 135° C. Over a period of 2 hours, 100 g (0.0389 moles) of CAPA®316 (polycaprolactone polyol sold by Interox Chemicals Ltd., having a molecular weight of 1000 and containing 3.89 equivalents of hydroxyl groups per kilogram of substance) are added dropwise. After cooling, the reaction product is a viscous liquid having a viscosity of 40 500 mPa·s (at 67° C.), a $T_g$ of −19° C. and containing 2.41 equivalents of free carboxyl groups per kilogram of polymer.

EXAMPLE 5

Preparation of a Half-Ester of a Polyester Polyol and Succinic Anhydride 100 g of K-Flex®148 (polyester polyol sold by King Industries Inc., based on linear aliphatic polycarboxylic acids and polyols having a viscosity of 4000 mPa·s at 25° C. and 4.16 equivalents of free hydroxyl groups per kilogram of substance), together with 42.2 g of succinic anhydride and 1.4 g of tripropylamine, are charged to a reactor fitted with mechanical stirrer, nitrogen sparge and thermometer, and the mixture is heated to 135° C. The resultant liquid has a viscosity of 7800 Pa·s (at 67° C.), a $T_g$ of −27° C. and contains 2.94 equivalents of free carboxyl groups and is not further purified.

EXAMPLE 6

A clear lacquer solution is prepared by mixing the following components:

| Components | Amount [g] |
|---|---|
| methacrylate component of Example 1 | 32.8 |
| half-ester of Example 5 | 14.0 |
| triglycidyl trimellitate (6.82 eq/kg) | 17.0 |
| cyclohexanone | 36.2 |

The solution is applied to a substrate with an applicator, dried, and cured at 180° C. for 30 minutes. The coating has a thickness of 30 μm and has the following properties:

| | |
|---|---|
| Erichsen test (DIN 53 156) | 10.0 mm |
| impact strength R[3] | 160 kg · cm |
| P4ersoz hardness | 244 s |
| acetone test | 2.5 |

[3]The impact strength is determined by dropping a die of known mass from a specific height on to the coated substrate. The indicated value is the product of the mass of the die in kg and the greatest height in cm at which the coating still remains undamaged, i.e. at which no cracks in the coating can be observed at 10-fold magnification. The letter "E" denotes that the die strikes the side of the substrate adjacent to the coating, whereas the letter "D" denotes that the die strikes the coated side.

The acetone test is carried out as rub test as follows: A ball of cottonwool is impregnated with acetone and rubbed 20 times over a portion of the coated surface back and forth. The result is evaluated in accordance with the following 5 point scale (DIN 53 320): 0=unchanged; 1=no softening, coating cannot be scratched with the finger nail: 2=coating just scratchable, cottonwool may be stained; 3=softened, easily scratchable; 4=onset of dissolution; 5=complete dissolution.

EXAMPLE 7

A clear lacquer solution is prepared by mixing the following components at low shear:

| Components | Amount [g] |
|---|---|
| methacrylate component of Example 1 | 181.5 |
| half-ester of Example 4 | 60.0 |
| diglycidyl hexahydrophthalate (6.6 eq/kg) | 76.5 |
| flow control agent[1] | 0.75 |
| N-benzyldimethylamine catalyst | 3.0 |
| solvent[2] | 271.5 |

[1]Lo 50 ®, a silicone oil sold by Wacker Chemie, 10% in toluene
[2]mixture of 70% 1-methoxy-2-propanol, 20% 1-methoxy-2-propylacetate and 10% methyl isobutyl ketone.

The solids content of the lacquer solution is 53±1% by weight, and the viscosity at 25° C. is 150 mPa·s (ICI CONE & PLATE VISCOSIMETER). The solids content for a spray viscosity coresponding to 18 seconds flow time (No. 4 cup DIN) is 47% by weight. The clear lacquer is applied to an aluminium substrate and a Florida substrate (polyester/melamine laminate). After a cure of 30 minutes at 140° C. the coating has a layer thickness of 25 μm with the following properties:

| | Aluminum | Florida |
|---|---|---|
| Erichsen test [mm] | 9.9 | 5.8[4] |
| impact strength [kg · cm] D/R[3] | 160/100 | 80/80[4] |
| Persoz hardness [s] | 252 | 258 |
| acetone test[5] | 3/3 | 3/3 |
| adhesion test[6] | Gt0 | Gt0 |

[3]q.v. under Example 6
[4]Substrate breaks at this point
[5]First value determined in accordance with the particulars given in Example 6/second value in accordance with the same scale, but after immersion for 1 minute in acetone.
[6]Cross-cut adhesion test according to DIN 53 151: By means of precisely defined cutting devices a square cross-cut pattern is etched into the coating such that the distance of the individual lines of the pattern, depending on the thickness of the coating, must be 1, 2 or 3 millimetres. To evaluate the adhesive strength, the percentage of the segments of the cross-hatched area that peel off is assessed: Gt0 = 0%; Gt1 = c. 5%; Gt2 = c. 15%; Gt3 = c. 35%; Gt4 = 65% and more; Gt5 = 100%.

EXAMPLE 8

The procedure of Example 7 is repeated, but using the following lacquer formulation:

| Components | Amount [g] |
|---|---|
| methacrytlate component of Example 2 | 186,2 |
| half-ester of Example 4 | 60.0 |
| diglycidyl hexahydrophthalate (6.6 eq/kg) | 72.0 |
| flow control agent[1] | 0.75 |
| UV absorber CGL 400 (2%) | 6.4 |
| antioxidant Tinuvin ® 123 (1%) | 3,2 |
| 1,8-diazabicyclo[5,4,0]-7-undecene as catalyst | 5.8 |
| solvent[2] | 267.0 |

The lacquer so obtained has a solids content of 55% by weight. It is applied in a thickness of 35 μm to an aluminium substrate and a Florida substrate, each coated with a commercial automobile metal-effect lacquer (VWL 97 A/BASF).

After a 30 minute cure at 130° C. the 35 μm coating has the following properties:

| | Aluminium | Florida |
|---|---|---|
| Erichsen test [mm] | 9.6 | 6.1[4] |
| impact strength [kg · cm] D/R[3] | 160/160 | 80/80[4] |
| Persoz hardness [s] | 197 | 173 |
| acetone test[5] | 3/3 | 3/3 |
| adhesion test[6] | 0 | 0 |
| Yi[10]/gloss (20°)[9] | −0.9/94 | −2/82 |

| Yi/gloss (20°) | | |
|---|---|---|
| after 500 h weathering[7] | −1.6/89 | −2/86 |
| after 1900 h weathering | −2/84 | −2/85 |
| after 4400 h weathering | 0/54 | −1/54 |

[7]Accelerated weathering in a Weatherometer ATLAS CI 65, weathering cycle NBR 180
[9]Measurement of gloss at an angle of 20°
[10]Yellowness, determined with a spectral photometer according to DIN 6172

EXAMPLE 9

A pigmented finishing lacquer of the following composition is prepared:

| Components | Amount [g] |
|---|---|
| methacrylate component of Example 1 | 136.0 |
| half-ester of Example 3 | 64.0 |
| diglycidyl hexahydrophthalate (6.6 eq/kg) | 64.2 |
| titanium dioxide CRONOS ® 2160 | 113.2 |
| flow control agent[1] | 0.75 |
| N-benzyldimethylamine as catalyst | 2.65 |
| solvent[2] | 151.0 |

The lacquer has a solids content of 71% by weight and a viscosity of 600 mPa·s. The formulation is applied to a thickness of 30 μm to an aluminium substrate and the coating is cured for 30 minutes at the temperatures indicated in following Table. The following properties of the coating are found:

| | Cure at | | |
|---|---|---|---|
| | 100° C. | 120° C. | 140° C. |
| Erichsen test [mm] | 9.8 | 9.6 | 9.4 |
| impact strength [kg · cm] R[3] | <20 | 160 | 160 |
| Persoz hardness [s] | 76 | 176 | 197 |
| acetone test[5] | 3/4 | 3/3 | 3/3 |
| adhesion test[6] | Gt0 | Gt0 | Gt0 |
| Yi/gloss (60°)[8] | — | −3.3/89 | −3.1/87 |
| Yi/gloss (60°) | | | |
| after 2000 h weathering[7] | — | −2,5/85 | −2,5/86 |
| after 3300 h weathering | — | −2/52 | −3/53 |

[8]Measurement of gloss at an angle of 60°.

It is especially noteworthy that the gloss, despite the absence of a UV absorber and an antioxidant, decreases only very slightly even after 2000 h weathering.

EXAMPLE 10

A lacquer of the following composition is prepared:

| Components | Amount [g] |
|---|---|
| methacrylate component of Example 3 | 150 |
| half-ester of Example 4 | 50.0 |
| diglycidyl hexahydrophthalate (6.6 eq/kg) | 51.3 |
| Byk 300 | 1.4 |
| UV absorber CGL 400 (2%) | 5.0 |
| antioxidant Tinuvin ® 123 (1%) | 2.5 |

-continued

| Components | Amount [g] |
|---|---|
| 1,8-diazabicyclo[5,4,0]-7-undecene as catalyst | 7.5 |
| solvent[2] | 493.7 |

The lacquer so obtained has a solids content of 35% by weight and a viscosity of 40 mPa·s. It is applied to an aluminium substrate and a Florida substrate, each coated with a commercial automobile metal-effect lacquer (VWL 97 A/BASF).

After a 30 minute cure at 130° C. the coating has the following properties:

| | Aluminium | Florida |
|---|---|---|
| layer thickness [μm] | 25–35 | 35–40 |
| Erichsen test [mm] | 10.3 | 6.0[4] |
| impact strength [kg · cm] D/R[3] | 160/80 | 80/80[4] |
| Persoz hardness [s] | 136 | 134 |
| acetone test[5] | 3/3 | 3/3 |
| adhesion test[6] | Gt1 | Gt0 |
| Yi[10]/gloss (20°) | — | 0.3/84 |
| Yi/gloss (20°) | | |
| after 800 h weathering[7] | — | −2/85 |
| after 2400 h weathering | — | −2/54 |

EXAMPLE 11

A further curable clear lacquer, in particular for application to a primer/base coat system, has the following composition:

| Components | Amount [g] |
|---|---|
| methacrylate component of Example 1 | 260 |
| half-ester of Example 4 | 140 |
| triglycidyl trimellitate (6.82 eq/kg) | 124.2 |
| flow control agent[1] | 1.7 |
| UV absorber CGL 400 (2%) | 10.5 |
| antioxidant Tinuvin ® 123 (1%) | 5.2 |
| 1,8-diazabicyclo[5,4,0]-7-undecene as catalyst | 8.9 |
| solvent[2] | 350 |

The lacquer so obtained has a solids content of 61% by weight and a viscosity of 440 mPa·s. It is applied to an aluminium substrate and a Florida substrate and the coating is cured under the different conditions indicated in the following Tables. The following properties of the lacquer coatings (layer thickness 30–40 μm) are found:

| | Aluminium substrate | | |
|---|---|---|---|
| | Cure [temperature in ° C./time in min] | | |
| | 80/45 | 100/30 | 130/30 |
| Erichsen test [mm] | 10.2 | 9.6 | 8.4 |
| impact strength [kg · cm] D/R[3] | 160/120 | 160/100 | 160/60 |
| Persoz hardness [s] | 218 | 263 | 289 |

-continued

| | Aluminium substrate Cure [temperature in ° C./time in min] | | |
|---|---|---|---|
| | 80/45 | 100/30 | 130/30 |
| acetone test[5] | 3/3 | 3/0 | 3/0 |
| adhesion test[6] | Gt2 | Gt1-2 | Gt0 |

EXAMPLE 12

A clear lacquer of the following composition is prepared:

| Components | Amount [g] |
|---|---|
| methacrylate component of Example 1 | 234.8 |
| half-ester of Example 4 | 156.5 |
| triglycidyl trimellite (6.82 eq/kg) | 123.5 |
| flow control agent[1] | 1.7 |
| UV absorber CGL 400 (2%) | 10.3 |
| antioxidant Tinuvin ® 123 (1%) | 5.1 |
| 1,8-diazabicyclo[5,4,0]-7-undecene as catalyst | 8.6 |
| solvent[2] | 350 |

The lacquer so obtained has a solids content of 60% by weight and a viscosity of 400 mPa·s. The clear lacquer is applied to an aluminium substrate and a Florida substrate, each coated with an automobile metal-effect lacquer VWL 97 A/BASF. After a cure of 30 minutes at 130° C. the coatings have the following properties:

| Substrate | Aluminium | Aluminium coated | Florida coated |
|---|---|---|---|
| layer thickness [μm] | | 30 | 40 |
| Erichsen test [mm] | 8.7 | 9.3 | 5.3[4] |
| impact strength [kg · cm] D/R[3] | 160/120 | 160/160 | 80[4]/80[4] |
| Persoz hardness [s] | 276 | 264 | 180 |
| acetone test[5] | 0/3 | 0/3 | 0/3 |
| adhesion test[6] | Gt0 | Gt0 | Gt0 |
| Yi/gloss (20°) | — | 1.7/99 | 0,7/82 |
| Yi/gloss (20°) | | | |
| after 1000 h weathering[7] | — | 1/84 | −1/79 |
| after 1700 h weathering | — | — | −1/53 |
| after 2100 h weathering | — | 2/53 | — |

EXAMPLE 13

A lacquer formulation corresponding to that of Example 12 is prepared, but using the acrylic lacquer of Example 2. The lacquer so obtained is applied to an aluminium substrate and a Florida substrate, each coated with an automobile metal-effect lacquer VWL 97 A/BASF. After a cure of 30 minutes at 130° C. the coatings have the following properties (layer thickness 25 μm):

| Substrate | Aluminium | Florida coated |
|---|---|---|
| Erichsen test [mm] | 9.6 | 5.3[4] |
| impact strength [kg · cm] D/R[3] | 160/160 | 80[4]/80[4] |

-continued

| Substrate | Aluminium | Florida coated |
|---|---|---|
| Persoz hardness [s] | 249 | 187 |
| acetone test[5] | 0/3 | 0/3 |
| adhesion test[6] | Gt0 | Gt0 |
| Yi/gloss (20°) | — | −1.7/88 |
| Yi/gloss (20°) | | |
| after 1000 h weathering[7] | — | −1/86 |

EXAMPLE 14

A clear lacquer of the following composition is prepared:

| Components | Amount [g] |
|---|---|
| metacrylate component of Example 1 | 300 |
| half-ester of Example 4 | 100 |
| glycidylated trimethylolpropane having an epoxy value of 8 eq/kg | 105 |
| flow control agent[1] | 0.9 |
| UV absorber CGL 400 (2%) | 10.1 |
| antioxidant Tinuvin ® 123 (1%) | 5.05 |
| 1,8-diazabicyclo[5,4,0]-7-undecene as catalyst | 8.8 |
| solvent[2] | 372 |

The lacquer so obtained has a solids content of 58% by weight and a viscosity of 265 mPa·s. The clear lacquer is applied to an aluminium substrate and a Florida substrate, each coated with an automobile metal-effect lacquer VWL 97 A/BASF. After a cure of 30 minutes at 130° C. the coatings have the following properties:

| Substrate | Aluminium | Aluminium coated | Florida coated |
|---|---|---|---|
| layer thickness [μm] | 25–30 | 25 | 40 |
| Erichsen test [mm] | 9.6 | — | 5.3[4] |
| impact strength [kg · cm] D/R[3] | 160/160 | 160/160 | 80[4]/80[4] |
| Persoz hardness [s] | 196 | 159 | 150 |
| acetone test[5] | 3/3 | 3/3 | 3/3 |
| adhesion test[6] | Gt0 | Gt0 | Gt0 |
| Yi/gloss (20°) | — | −0.2/84 | −1.7/81 |
| Yi/gloss (20°) | | | |
| after 1000 h weathering[7] | — | −1/77 | −2/77 |
| after 3200 h weathering | | +1/51 | 0/54 |

EXAMPLE 15

A clear lacquer of the following composition is prepared:

| Components | Amount [g] |
|---|---|
| methacrylate component of Example 1 | 140 |
| half-ester of Example 4 | 60 |
| reaction product of glycidylated trimethylolpropane and isophorone diisocyanate having an epoxy value of 5.81 eq/kg | 73.4 |
| flow control agent[1] | 0.9 |
| UV absorber CGL 400 (2%) | 5.4 |
| antioxidant Tinuvin ® 123 (1%) | 2.7 |

-continued

| Components | Amount [g] |
|---|---|
| N-benzyldimethylamine as catalyst | 2.55 |
| solvent[2] | 220 |

The lacquer so obtained has a solids content of 56.5% by weight and a viscosity of 280 mPa·s. The clear lacquer is applied to an aluminium substrate and a Florida substrate, each coated with an automobile metal-effect lacquer VWL 97 A/BASF. After a cure of 30 minutes at 130° C. the coatings have the following properties:

| Substrate | Aluminium | Aluminium coated | Florida coated |
|---|---|---|---|
| layer thickness [μm] | 35–45 | 35–45 | 35–45 |
| Erichsen test [mm] | 9.2 | 9.0 | 5.5[4] |
| impact strength [kg · cm] D/R[3] | 160/40 | 160/60 | 80[4]/80[4] |
| Persoz hardness [s] | 267 | 187 | 173 |
| acetone test[5] | 0/0 | 0/3 | 0/3 |
| adhesion test[6] | Gt0 | Gt0 | Gt0 |
| Yi/gloss (20°) | −1.1/90 | | −2.4/87 |
| Yi/gloss (20°) | | | |
| after 500 h weathering[7] | — | 0/89 | −2/86 |
| after 2300 h weathering | — | — | −1/57 |
| after 4100 h weathering | — | +1/70 | — |

EXAMPLE 16

A clear lacquer of the following composition is prepared:

| Components | Amount [g] |
|---|---|
| methacrylate component of Example 1 | 140 |
| half-ester of Example 4 | 60 |
| reaction product of glycidylated trimethylolpropane and isophorone diisocyanate having an epoxy value of 6.64 eq/kg | 64.2 |
| flow control agent[1] | 0.9 |
| UV absorber CGL 400 (2%) | 5.3 |
| antioxidant Tinuvin ® 123 (1%) | 2.6 |
| N-benzyldimethylamine as catalyst | 2.4 |
| solvent[2] | 220 |

The lacquer so obtained has a solids content of 55.3% by weight and a viscosity of 210 mPa·s. The clear lacquer is applied to an aluminium substrate and a Florida substrate, each coated with an automobile metal-effect lacquer VWL 97 A/BASF. After a cure of 30 minutes at 130° C. the coatings have the following properties (layer thickness 30–35 μm):

| Substrate | Aluminium | Florida coated |
|---|---|---|
| Erichsen test [mm] | 10.3 | 5.7[4] |
| impact strength [kg · cm] D/R[3] | >140/>120 | 80/80 |
| Persoz hardness [s] | 234 | 236 |
| acetone test[5] | 0/3 | 0/3 |
| adhesion test[6] | Gt0 | Gt0 |
| Yi/gloss (20°) | — | −1.4/86 |
| Yi/gloss (20°) | | |

-continued

| Substrate | Aluminium | Florida coated |
|---|---|---|
| after 1000 h weathering[7] | — | −1/82 |
| after 2800 h weathering | — | −1/52 |

EXAMPLE 17

The procedure of Example 16 is repeated, except for the addition of 4.8 g of 1,8-diazabicyclo[5,4,0]-7-undecene as catalyst. The following properties are found (layer thickness 30–40 μm):

| Substrate | Aluminium | Florida coated |
|---|---|---|
| Erichsen test [mm] | 9.0 | 5.9[4] |
| impact strength [kg · cm] D/R[3] | 160/80 | 80/80 |
| Persoz hardness [s] | 236 | 159 |
| acetone test[5] | 0/3 | 0/3 |
| adhesion test[6] | Gt0 | Gt0 |
| Yi/gloss (20°) | — | −1/84 |
| Yi/gloss (20°) | | |
| after 1000 h weathering[7] | — | −2/81 |
| after 3300 h weathering | — | 0/54 |

EXAMPLE 18

Preparation of the Triglycidyl Ester of 1,2,4-Cyclohexyltricarboxylic Acid 1,2,4-Cyclohexyltricarboxylic acid (conveniently obtainable by hydrogenation of trimellitic acid in accordance with the teaching of U.S. Pat. No. 3,444,237) is glycidylated using an apparatus which permits the use of epichlorohydrin as entrainer for the water separation under reduced pressure. This apparatus consists of a 250 ml reactor which can be heated externally and is fitted with mechanical stirrer, thermometer, an efficient multiple-coil condenser and two dropping funnels with pressure equaliser. Also connected are a water-jet pump and a water separator which makes it possible to recycle unused epichlorohydrin to the reactor.

20 g of 1,2,4-cyclohexyltricarboxylic acid, 152 ml of epichlorohydrin and 1.6 g of a 50% aqueous solution of tetramethylammonium chloride are heated to c. 80° C. With good stirring, a vacuum is cautiously applied to the apparatus until the epichlorohydrin refluxes vigorously. The pH of the reaction mixture is constantly monitored and the mixture is allowed to react further until it becomes basic. The reaction mixture is then cooled to 50° C. and a pressure of 0.11 bar (80 mm Hg) is applied. Over the course of 3 hours, 24.28 g of a 50% solution of sodium hydroxide are added dropwise from the second dropping funnel while keeping the temperature at c. 46 to 50° C. The water introduced and formed, together with the epichlorohydrin, is distilled off as an azeotropic mixture. The epichlorohydrin separated from the water in the water separator is continuously recycled to the reaction mixture. When the dropwise addition of sodium hydroxide is complete, the reaction mixture is kept for a further hour at c. 46° C. A total of c. 15 g of water are removed. The resultant suspension is afterwards filtered under normal pressure over kieselgur as filter aid. The residual reaction mixture in the reactor is taken up in ethyl acetate and likewise filtered, and the filter cake is washed with ethyl acetate. The combined filtrates are extracted with 10% sodium hydrogenphosphate solution and the extracted mixture is concentrated at 80° C. under vacuum on a rotary evaporator. The last traces of solvent are afterwards removed over 20 minutes at 120° C and under a high vacuum.

The desired product is obtained as a viscous liquid (4750 mPa·s at 25° C.) and has an epoxy value of 7.44 eq/kg of substance. Its molecular weight ($M_w$) is found by GPC to be 335 ($M_w/M_n$=1.093).

EXAMPLE 19

A clear lacquer of the following composition is prepared:

| Components | Amount [g] |
| --- | --- |
| methacrylate component of Example 2 | 153.9 |
| half-ester of Example 4 | 102.6 |
| epoxy resin of Example 18 | 47 |
| flow control agent[1] | 1.1 |
| UV absorber CGL 400 (2%) | 6.1 |
| antioxidant Tinuvin ® 123 (1%) | 3,0 |
| 1,8-diazabicyclo[5,4,0]-7-undecene | 5.3 |
| solvent[2] | 206.1 |

The lacquer so obtained has a solids content of 59.5% by weight and a viscosity of 600 mPa·s. The clear lacquer is applied to an aluminium substrate and a Florida substrate, each coated with an automobile metal-effect lacquer VWL 97 A/BASF. After a cure of 30 minutes at 130° C. the coatings have the following properties (layer thickness 25 μm):

| Substrate | Aluminium | Florida coated |
| --- | --- | --- |
| Erichsen test [mm] | 10.3 | 4.8[4] |
| impact strength [kg · cm] D/R[3] | 160/160 | 80/80 |
| Persoz hardness [s] | 197 | 171 |
| acetone test[5] | 3/3 | 3/3 |
| adhesion test[6] | Gt0 | Gt0 |
| Yi/gloss (20°) | — | −0.3/85 |
| Yi/gloss (20°) | | |
| after 2000 h weathering[7] | — | −1/58 |

EXAMPLE 20

A clear lacquer of the following composition is prepared:

| Components | Amount [g] |
| --- | --- |
| commercial methacrylate component Joncryl ® SCX817C (0.982 eqCOOH/kg) | 280 |
| half-ester of Example 4 | 120 |
| diglycidyl hexahydrtophthalate (6.6 eq/kg) | 81.7 |
| flow control agent (Byk ® 300) | 1.6 |
| UV absorber CGL 400 (2%) | 9.6 |
| antioxidant Tinuvin ® 123 (1%) | 4.8 |
| 1,8-diazabicyclo[5,4,0]-7-undecene | 8.4 |
| solvent[2] | 336 |

The lacquer so obtained has a solids content of 60.1% by weight and a viscosity of 1160 mPa·s. The clear lacquer is applied to an aluminium substrate and a Florida substrate, each coated with an automobile metal-effect lacquer VWL 97 A/BASF. After a cure of 30 minutes at 130° C. the coatings have the following properties (layer thickness 30 μm):

| Substrate | Aluminium | Florida coated |
| --- | --- | --- |
| Erichsen test [mm] | 10.3 | 5.4[4] |
| impact strength [kg · cm] D/R[3] | 160/100 | 80/80 |
| Persoz hardness [s] | 252 | 240 |
| acetone test[5] | 3/3 | 3/3 |
| adhesion test[6] | Gt0 | Gt0 |
| Yi/gloss (20°) | — | −1/87 |
| Yi/gloss (20°) | | |
| after 2600 h weathering[7] | — | −1/80 |

EXAMPLE 21

A clear lacquer of the following composition is prepared:

| COmponents | Amount [g] |
| --- | --- |
| commercial methacrylate component Joncryl ® SCX817C (0.982 eqCOOH/kg) | 280 |
| half-ester of Example 4 | 120 |
| mixture of | 85.2 |
| 70 parts by wt of glycidyl hexahydrophthalate/ | |
| 30 parts by wt of triglycidyl trimellite | |
| (6.86 eq/kg) | |
| flow control agent (Byk ® 300) | 1.0 |
| UV absorber CGL 400 (2%) | 9.6 |
| antioxidant Tinuvin ® 123 (1%) | 4.8 |
| 1,8-diazabicyclo[5,4,0]-7-undecene | 8.2 |
| solvent[2] | 335.4 |

The lacquer so obtained has a solids content of 60.3% by weight and a viscosity of 1120 mPa·s. The clear lacquer is applied to an aluminium substrate and a Florida substrate, each coated with an automobile metal-effect lacquer VWL 97 A/BASF. After a cure of 30 minutes at 130° C. the coatings have the following properties (layer thickness 40 μm):

| Substrate | Aluminium | Florida coated |
| --- | --- | --- |
| Erichsen test [mm] | 10.3 | 5.7[4] |
| impact strength [kg · cm] D/R[3] | — | 80/60−70 |
| Persoz hardness [s] | 289 | 266 |
| acetone test[5] | 3/0−1 | 3/0−1 |
| adhesion test[6] | Gt0 | Gt1 |
| Yi/gloss (20°) | — | −1/85 |
| Yi/gloss (20°) | | |
| after 2000 h weathering[7] | — | −1/80 |

What is claimed is:
1. A curable composition consisting essentially of
A) a mixture of
A1) at least one polymer based on acrylate and/or methacrylate monomers and containing on average 0.1 to 4.0 equivalents of free carboxyl groups per kilogram of polymer, and
A2) at least one carboxyl-terminated polyester which contains on average 0.2 to 6 equivalents of free carboxyl groups per kilogram of polyester such that component A1) constitutes 50 to 90% by weight, and component A2) makes up the remainder of the mixture A, wherein component A2) is a half-ester of a polylactone having the structural formula

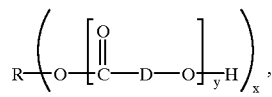

wherein R is the radical of a cyclic or acyclic polyol $R(OH)_x$ of valency x without its hydroxyl groups, x is an integer of at least 2, y is 1 or an integer greater than 1, and D corresponds to an alkylene group of structure

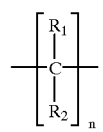

containing a maximum number of 12 carbon atoms, and wherein $R_1$ and $R_2$ are each independently of the other a hydrogen atom or a $C_1$–$C_3$ alkyl radical, and n is an integer from 5 to 8, which half-ester has a molecular weight of 500 to 5000 and a glass transition temperature below 30° C.;

B) a polyglycidyl ester of a cycloaliphatic polycarboxylic acid or a mixture of two or more than two of said polyglycidyl esters of cycloaliphatic polycarboxylic acids;

C) a catalyst for speeding up the thermal reaction of epoxy and carboxyl groups, and D) an inert solvent;

the molar ratio of free carboxyl groups to epoxy groups in said composition being 0.5:1 to 1.5:1, and said composition containing, except for component B), no components carrying epoxy groups.

2. A composition according to claim 1, which contains an epoxy resin selected from the group consisting of cis-hexahydrophthalic acid diglycidyl ester, trimellitic acid triglycidyl ester and 1,2,4-cyclohexantricarboxylic acid triglycidyl ester.

3. A composition according to claim 1, which contains an epoxy resin containing three or more epoxy groups per molecule.

4. A composition according to claim 1, wherein n is 5 and $R_1$ and $R_2$ are each a hydrogen atom.

5. A composition according to claim 1, wherein x is 2 or 3.

* * * * *